United States Patent
MacDonald et al.

(10) Patent No.: US 7,528,150 B2
(45) Date of Patent: *May 5, 2009

(54) UREA DERIVATIVES HAVING VANILLOID RECEPTOR ANTAGONIST ACTIVITY

(75) Inventors: Gregor James MacDonald, Harlow (GB); Harshad Kantilal Rami, Harlow (GB); Mervyn Thompson, Harlow (GB)

(73) Assignee: Glaxo Group Limited, Greenford, Middlesex (GB)

(*) Notice: Subject to any disclaimer, the term of this patent is extended or adjusted under 35 U.S.C. 154(b) by 506 days.

This patent is subject to a terminal disclaimer.

(21) Appl. No.: 10/548,133

(22) PCT Filed: Mar. 4, 2004

(86) PCT No.: PCT/EP2004/002376

§ 371 (c)(1), (2), (4) Date: Sep. 6, 2005

(87) PCT Pub. No.: WO2004/078101

PCT Pub. Date: Sep. 16, 2004

(65) Prior Publication Data

US 2006/0178397 A1    Aug. 10, 2006

(30) Foreign Application Priority Data

Mar. 8, 2003    (GB) ................. 0305426.9

(51) Int. Cl.
  *C07D 401/02* (2006.01)
  *A61K 31/47* (2006.01)

(52) U.S. Cl. ........................ 514/310; 546/143
(58) Field of Classification Search ........................ None
See application file for complete search history.

(56) References Cited

U.S. PATENT DOCUMENTS

| | | | |
|---|---|---|---|
| 5,925,635 | A | 7/1999 | Maduskuie, Jr. et al. |
| 6,355,631 | B1 | 3/2002 | Achard et al. |
| 6,506,572 | B2 | 1/2003 | Biedermann et al. |
| 6,602,882 | B1 | 8/2003 | Davies et al. |
| 6,723,730 | B2 | 4/2004 | Bakthavatchalam et al. |
| 6,903,085 | B1 | 6/2005 | Thom et al. |
| 2003/0153568 | A1 | 8/2003 | Cusack et al. |
| 2004/0082661 | A1 | 4/2004 | Rami et al. |
| 2004/0171639 | A1 | 9/2004 | Rami et al. |
| 2005/0113414 | A1 | 5/2005 | Watson et al. |

FOREIGN PATENT DOCUMENTS

| | | |
|---|---|---|
| DE | 28 16 885 | 11/1978 |
| DE | 199 55 794 | 5/2000 |
| EP | 0416581 | 3/1991 |
| EP | 0591030 | 4/1994 |
| EP | 0625507 | 11/1994 |
| EP | 0628310 | 12/1994 |
| ES | 2007808 | 7/1989 |
| WO | WO 99/07672 A1 * | 2/1999 |
| WO | WO 00/21952 A1 * | 4/2000 |
| WO | WO00/71171 | 11/2000 |
| WO | WO01/07409 | 2/2001 |
| WO | WO 01/12188 A1 * | 2/2001 |
| WO | WO03/022809 | 3/2003 |
| WO | WO03/072545 | 9/2003 |
| WO | WO2004/024710 | 3/2004 |
| WO | WO2004/026836 | 4/2004 |
| WO | WO2004/078744 | 9/2004 |
| WO | WO2004/078749 | 9/2004 |

OTHER PUBLICATIONS

Frigola et al., *Journal of Medicinal Chemistry* vol. 36 No. 7 1993 pp. 801-810.
Carling et al., *Journal of Medicinal Chemistry* vol. 42 No. 14 (1999) pp. 2706-2715.
Huang et al., *Journal of Medicinal Chemistry* vol. 41 No. 13 (1998) pp. 2361-2370.
Huang et al., *Journal of Medicinal Chemistry* vol. 44 No. 25 (2001) pp. 4404-4415.

* cited by examiner

*Primary Examiner*—Zinna N Davis
(74) *Attorney, Agent, or Firm*—Reid S. Willis; Charles M. Kinzig

(57) ABSTRACT

According to the invention there are provided compounds of formula (I)

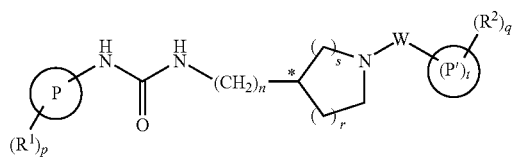

wherein $R^1$, p, P, n, s, r, W, P', t, $R^2$ and q are as defined in the specification, processes for preparing them and their use in therapy.

15 Claims, No Drawings

UREA DERIVATIVES HAVING VANILLOID RECEPTOR ANTAGONIST ACTIVITY

This application is a 371 of PCT/EP04/02376 filed Mar. 4, 2004.

This invention relates to novel compounds, especially urea derivatives, having pharmacological activity, processes for their preparation, to compositions containing them and to their use in medicine, especially in the treatment of various disorders.

Vanilloids are a class of natural and synthetic compounds that are characterised by the presence of a vanillyl (4-hydroxy 3-methoxybenzyl) group or a functionally equivalent group. Vanilloid Receptor (VR1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (*Tetrahedron*, 53, 1997, 4791) and olvanil or -N-(4-hydroxy-3-methoxybenzyl)oleamide (*J. Med. Chem.*, 36, 1993, 2595).

U.S Pat. Nos. 3,424,760 and 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively.

International Patent Applications, Publication Numbers WO 02/08221, WO 02/16317, WO 02/16318 and WO 02/16319 each disclose certain vanilloid receptor antagonists and their use in the treatment of diseases associated with the activity of the vanilloid receptor.

International Patent Applications, Publication Numbers WO 02/072536 and WO 02/090326, and International Patent Application, Publication Number WO 03/022809 (published after the priority date of the present application) disclose a series of urea derivatives and their use in the treatment of diseases associated with the activity of the vanilloid receptor.

According to a first aspect of the present invention, there is provided a compound of formula (I):

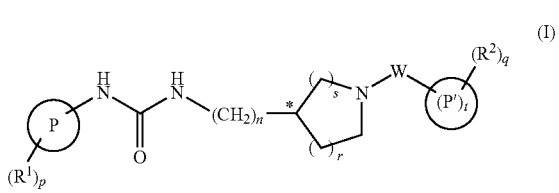

or a pharmaceutically acceptable salt or solvate thereof, wherein:
P and P' are independently selected from aryl and heteroaryl;
$R^1$ and $R^2$ are independently selected from H, halo, alkyl, alkoxy, cycloalkyl, aralkyl, aralkoxy, cycloalkylalkyl, cycloalkylalkoxy, —CN, —$NO_2$, —OH, —$OCF_3$, —$CF_3$, —$NR^4R^5$, —$S(O)_mR^6$, —$S(O)_2NR^4R^5$, —$OS(O)_2R^6$, —$OS(O)_2CF_3$, —$O(CH_2)_xNR^4R^5$, —$C(O)CF_3$, —C(O) alkyl, —C(O)cycloalkyl, —C(O)aralkyl, —C(O)Ar, —$(O)(CH_2)_xOR^6$, —$C(O)(CH_2)_xNR^4R^5$, —C(O)alkoxy, —$C(O)NR^4R^5$, —$(CH_2)_xC(O)$alkoxy, —$(CH_2)_xOC(O)$ $R^6$, —$(CH_2)_xOR^6$, —$(CH_2)_xNR^4R^5$, —$(CH_2)_xC(O)$ $NR^4R^5$, —$(CH_2)_xN(R^4)C(O)R^6$, —$(CH_2)_xS(O)_2NR^4R^5$, —$(CH_2)_xN(R^4)S(O)_2R^6$, -ZAr, —$(CH_2)_xS(O)_2R^6$, —$(OCH_2)_xS(O)_2R^6$, —$N(R^4)S(O)_2R^6$, —$N(R^4)C(O)R^6$ or —$(CH_2)_xC(O)$alkyl;
$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms;
Z represents O, S or $NR^7$;
W represents a group $CHR^3$ or $(CH_2)CHR^3$;
$R^3$ represents hydrogen or alkyl;
$R^6$ represents alkyl or aryl;
$R^7$ represents hydrogen, alkyl or aryl;
m represents and integer 1 or 2;
n represents and integer 0, 1, 2 or 3;
p and q independently represent an integer 0, 1, 2, 3 or 4;
r represents an integer 0, 1, 2 or 3;
s represents an integer 0, 1 or 2;
t represents 1; and
x represents an integer 0, 1, 2, 3, 4, 5 or 6.

Preferably W represents $CHR^3$.
Preferably P' represents phenyl or pyridyl (eg pyrid-2-yl), especially phenyl.
Preferably $R^4$ represents methyl or hydrogen
Preferably $R^5$ represents methyl or hydrogen.
Preferably $R^6$ represents methyl.
Preferably $R^7$ represents methyl or hydrogen.
Preferably Z represents a bond.
Preferably, x represents 1, 2 or 3.
Preferably, m represents 1.

Most particularly a preferred subset of compounds are defined by compounds of formula (IA):

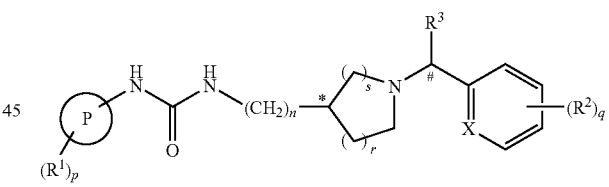

or a pharmaceutically acceptable salt or solvate thereof, wherein:
P, $R^1$, p, n, s, r, q, $R^2$ and $R^3$ are as defined above; and
X represents CH or N.
Preferably X represents CH.

The following preferences apply to compounds of formula (I) and formula (IA):
Preferably, P represents iso-quinolinyl. More preferably, P represents 5-isoquinolinyl.
Preferably, $R^1$ represents alkyl especially methyl.
Preferably, p represents 1 or 2, especially 1.
Preferably, n represents 0 or 1, especially 0.
Preferably $R^2$ represents H, halo or $CF_3$, more preferably H, chloro, fluoro or —$CF_3$, particularly chloro, fluoro or $CF_3$. Other $R^2$ groups of interest include t-Bu and —CN.
Preferably, $R^3$ represents H or methyl, especially hydrogen.

Preferably q represents 1 or 2.

Preferably, r+s represents 1, 2, 3 or 4, more preferably 1, 2 or 3, particularly 2 or 3, especially 2. Preferably r is 1. Preferably s is 1 or 2, especially 1.

Compounds in which r+s represents 1 especially those in which r is 0 and s is 1 are also of interest.

When p or q represent 2, 3 or 4, the groups $R^1$ or $R^2$ may be the same or different.

Particular groups which $(R^1)_pP$ may represent include 3-methyl-isoquinolin-5-yl and 1-methyl-isoquinolin-5-yl.

Particular groups which $(R^2)_qP'$ may represent include 2-Cl-phenyl, 2-CF$_3$-phenyl, 3-F-phenyl, 3,4-diCl-phenyl, 3,4-diF-phenyl, 3-Cl-5-CF$_3$-pyridin-2-yl. Other examples include phenyl, 2-F-phenyl, 4-F-phenyl, 4-CN-phenyl, 4-Cl-phenyl, 3-Cl-4-F-phenyl, 3-Cl-phenyl, 4-t-Bu-phenyl, 3-CF$_3$-phenyl, 4-CF$_3$-phenyl, 2-CN-phenyl, 3-CN-phenyl, 2,3-diF-phenyl.

While the preferred groups for each variable have generally been listed above separately for each variable, preferred compounds of this invention include those in which several or each variable in formula (I) or formula (IA) is selected from the preferred, more preferred, or most preferred groups for each variable. Therefore, this invention is intended to include all combinations of preferred, more preferred, and most preferred groups.

Compounds of formula (I) of particular interest according to the present invention are Examples 1-25 or pharmaceutically acceptable salts or solvates thereof.

Examples of the C$_{3-6}$azacycloalkane ring that $R^4$ and $R^5$ may independently represent, when taken together with the atoms to which they are attached, include pyrrolidine and piperidine.

Examples of the C$_{3-6}$(2-oxo)azacycloalkane ring that $R^4$ and $R^5$ may independently represent, when taken together with the atoms to which they are attached, include pyrrolidinone and piperidinone.

Examples of the C$_{5-8}$ polymethylene chain optionally interrupted by heteroatoms that $R^4$ and $R^5$ may independently represent when taken together with the atoms to which they are attached, include a C$_{5-8}$ polymethylene chain optionally interrupted by heteratoms such as O or —NR$^7$. Specific examples include morpholine and piperazine.

Certain of the carbon atoms of formula (I) are chiral carbon atoms, such as the carbon atoms marked with an "*" or "#", and therefore compounds of formula (I) may exist as stereoisomers. The invention extends to all optical isomers such as stereoisomeric forms of the compounds of formula (I) including enantiomers, diastereomers and mixtures thereof, such as racemates. The different stereoisomeric forms may be separated or resolved one from the other by conventional methods or any given isomer may be obtained by conventional stereospecific or asymmetric syntheses.

Preferred compounds of formula (I) have the C* carbon in the R-configuration.

Certain of the compounds herein can exist in various tautomeric forms and it is to be understood that the invention encompasses all such tautomeric forms.

As indicated above, the compounds of formula (I) can form salts, especially pharmaceutically acceptable salts. Suitable pharmaceutically acceptable salts are those use conventionally in the art and include those described in *J. Pharm. Sci.*, 1977, 66, 1-19, such as acid addition salts.

Suitable pharmaceutically acceptable salts include acid addition salts.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and if crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

As used herein the term "alkyl" as a group or part of a group refers to a straight or branched chain saturated aliphatic hydrocarbon radical containing 1 to 12 carbon atoms, suitably 1 to 6 carbon atoms. Such alkyl groups in particular include methyl ("Me"), ethyl ("Et"), n-propyl ("Pr'"), iso-propyl ("Pr''"), n-butyl ("Bu''''"), sec-butyl ("Bu'''"), tert-butyl ("Bu''"), pentyl and hexyl. The term "cycloalkyl" as part of a group refers to a saturated alicyclic hydrocarbon radical containing 3 to 12 carbon atoms, suitably 3 to 6 carbon atoms. Where appropriate, such alkyl groups may be substituted by one or more groups selected from halo (such as fluoro, chloro, bromo), —CN, —CF$_3$, —OH, —OCF$_3$, C$_{2-6}$ alkenyl, C$_{3-6}$ alkynyl, C$_{1-6}$ alkoxy, aryl and di-C$_{1-6}$ alkylamino. Preferably alkyl is unsubstituted.

As used herein, the term "alkoxy" as a group or part of a group refers to an alkyl ether radical, wherein the term "alkyl" is defined above. Such alkoxy groups in particular include methoxy, ethoxy, n-propoxy, iso-propoxy, n-butoxy, iso-butoxy, sec-butoxy and tert-butoxy. Where appropriate, such alkoxy groups may be substituted by one or more groups selected from halo (such as fluoro, chloro, bromo), —CN, —CF$_3$, —OH, —OCF$_3$, C$_{1-6}$ alkyl, C$_{2-6}$ alkenyl, C$_{3-6}$ alkynyl, aryl and di-C$_{1-6}$ alkylamino. Preferably alkoxy is unsubstituted.

As used herein, the term "aryl" as a group or part of a group refers to a carbocyclic aromatic radical ("Ar"). Suitably such aryl groups are 6 membered monocyclic groups or 8-10 membered fused bicyclic groups (including aromatic ring systems fused with non-aromatic ring systems), especially phenyl ("Ph"), biphenyl, indene and naphthyl, particularly phenyl.

Aryl groups contained within moieties $R^1$, $R^2$, $R^6$ or $R^7$ may optionally be substituted (and in the case of bicyclic groups containing an aromatic system fused with a non-aromatic systems may optionally be substituted on either or both of the aromatic and the non-aromatic portion) with one or more substituents selected from the list consisting of halo, hydroxy, carbonyl, alkoxy, alkyl, —CF$_3$, NR$^4$R$^5$ and —SO$_2$R$^6$.

As used herein, the term "heteroaryl" as a group or part of a group refers to a stable 5- 7-membered monocyclic or 7- to 10-membered bicyclic heterocyclic aromatic ring (including an aromatic ring system fused with a non-aromatic ring system) which consists of carbon atoms and from 1 to 4 heteroatoms independently selected from the group consisting of N, O and S. It is preferred that the total number of S and O atoms in the aromatic heterocycle is not more than 1. Examples of suitable heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolyl, carbazolyl, carbolinyl, chromanyl, chromenyl, cinnolinyl, decahydroquinolinyl, 2H, 6H-1,5,2-dithiazinyl, dihydrobenzofuranyl, furanyl, furazanyl, imidazolyl, 1H-indazolyl, indolinyl, indolyl, isobenzofuranyl, isochromanyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phthalazinyl, pteridinyl, purinyl, pyrazinyl, pyrazolyl, pyridooxazolyl, pyridoimidazolyl, pyridothiazolyl, pyridyl, pyrrolyl, quinazolinyl, quinolinyl, quinoxalinyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl.

The term "halo" is used herein to describe, unless otherwise stated, a group selected from fluorine ("fluoro"), chlorine ("chloro"), bromine ("bromo") or iodine ("iodo").

The term "naphthyl" is used herein to denote, unless otherwise stated, both naphth-1-yl and naphth-2-yl groups.

The term "pyridyl" includes 2-pyridyl, 3-pyridyl and 4-pyridyl but preferably denotes 2-pyridyl. The term pyrimidinyl includes 2-pyrimidinyl.

The present invention also provides a process for the preparation of a compound of formula (I) or a pharmaceutically acceptable salt thereof, which process comprises coupling a compound of formula (II):

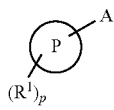

in which $R^1$, P and p are as defined in formula (I) with a compound of formula (III):

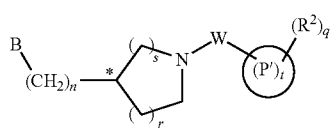

in which P', $R^2$, W, n, q, r, s and t are as defined in formula (I) and A and B contain appropriate functional groups which are capable of reacting together to form the urea moiety;

and thereafter, as necessary, carrying out one or more of the following reactions:
(i) converting one compound of formula (I) into another compound of formula (I);
(ii) removing any protecting group;
(iii) preparing a salt or a solvate of the compound so formed.

Suitable examples of appropriate A and B groups include:
(a) A is —N=C=O and B is $NH_2$; or A is $NH_2$ and B is N=C=O or
(b) A is $NH_2$ and B is $NH_2$ together with an appropriate urea forming agent.

In process (a) the reaction is typically carried out in an inert solvent such as dichloromethane or acetonitrile.

In process (b) the urea forming agent can be carbonyl diimidazole or phosgene or triphosgene, and carried out in an inert organic solvent such as diethyl ether, tetrahydrofuran or DCM at ambient or elevated temperature in the presence of a base such as triethylamine or pyridine.

An alternative method of synthesis of the unsymmetrical urea compounds of formula (I) is from a diaryl carbonate, via the corresponding carbamate. Such a methodology is described by Freer et al. (Synthetic Communications, 26(2), 331-349, 1996). It would be appreciated by those skilled in the art that such a methodology could be readily adapted for preparation of the compounds of formula (I).

A further method of synthesis of compounds of formula (I) is using phenyl chloroformate as described by B. R. Baker et al., J. Med. Chem., 1969, 12, 672-6.

A compound of formula (III) may be prepared by reaction of a compound of formula (IV):

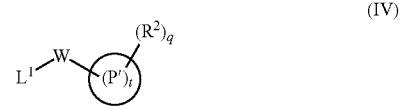

wherein, P', W t, q and $R^2$ as defined above and $L^1$ is a leaving group, with a compound of formula (V):

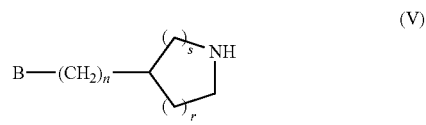

wherein B, n, r and s are as defined above, or a protected derivative thereof. When B represents an amine group, preferably it is employed as a protected derivative; examples of amine protecting groups are mentioned below.

Suitably $L^1$ is a halogen, such as chlorine.

Suitably, the compound of formula (V) is in an activated form, for example an ionic form. Such activated forms are prepared using conventional coupling reaction methodology, as for example by reacting compounds (IV) and (V) in the presence of an alkali carbonate, such as potassium carbonate, in an aprotic solvent such as dimethylformamide using reaction conditions appropriate to the particular methodology chosen, for example at an elevated temperature, such as 100° C.

Compounds of formulae (IV) and (V) are commercially available, or are prepared by known procedures, such as those disclosed in: Heterocycles, 1984, 22(1), 117 and J. Chem. Soc., Perkin 1, 1988, 4, .921 for compounds of formula (IV) and J. Med. Chem., 1992, 35(10), 1764 for compounds of formula (V), or by methods analogous to these disclosed methods.

Compounds of formula (II) are either known or may be prepared by known methods, or methods analogous to those described herein.

The present invention also provides a process for the preparation of a compound of formula (IA) or a pharmaceutically acceptable salt or solvate thereof, which process comprises reacting a compound of formula (IIA):

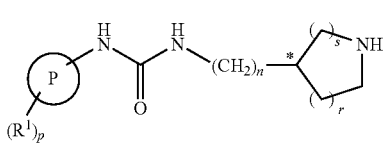

in which $R^1$, P, n, p, s and r are as defined in formula (I) with a compound of formula (IIIA):

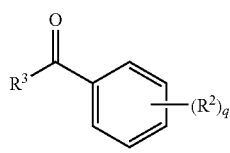

in which q, $R^2$ and $R^3$ are as defined in formula (IA), in the presence of a reducing agent and thereafter, as necessary, carrying out one or more of the following reactions:
(i) converting one compound of formula (I) into another compound of formula (I);
(ii) removing any protecting group;
(iii) preparing a salt or a solvate of the compound so formed.

A suitable reducing agent is sodium triacetoxyborohydride.

The reaction between the compounds of formulae (IIA) and (IIIA) is carried out in a suitable solvent under conventional conditions for reductive alkylation, at a suitable temperature providing a suitable rate of formation of the required product, over a suitable reaction time. A suitable solvent is dichloromethane. Suitable reaction temperatures include those in the range of 20° C. to 100° C., preferably room temperature. Suitable reaction times are those in the range 12-72 hours. The reaction products are isolated using conventional methods, such as column chromatography.

Compounds of formula (IIA), may be prepared by reaction of a compound of formula (II),

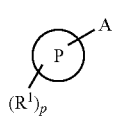

in which $R^1$, P and p are as defined in formula (I) with a compound of formula (IV),

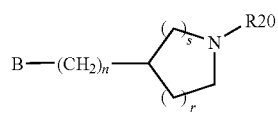

in which n, r and s are as defined in formula (I) and A and B contain appropriate functional groups which are capable of reacting together to form the urea moiety and R20 is a suitable amino protecting group such as benzyl or tert butyloxycarbonyl as mentioned below.

Suitable examples of appropriate A and B groups are as mentioned above in relation to the reaction of compounds of formula (II) and (III).

Compounds of formula (IIIA) are either known per se or may be prepared by known methods.

The above-mentioned conversions of a compound of formula (I) into another compound of formula (I) includes any conversion which may be effected using conventional procedures, but in particular the said conversions include any combination of:
(i) converting one group $R^1$ into another group $R^1$;
(ii) converting one group $R^2$ into another group $R^2$.

The above-mentioned conversions (i) and (ii) may be carried out using any appropriate method, such as those described in Larock R. F. 'Comprehensive Organic Transformations", New York, Wiley (1999), under conditions determined by the particular groups chosen.

The above-mentioned conversions (i) and (ii) may as appropriate be carried out on any of the intermediate compounds mentioned herein.

It will be appreciated that it may be necessary to protect certain reactive substituents during some of the above-mentioned procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

In particular in the reaction of compounds of formula (IV) and (V) to form compounds of formula (III) the group B preferably represents —NH(t-BOC)—.

In the reaction of compounds of formula (II) and (IV) to form compounds of formula (IIA), B preferably represents —$NH_2$ and the ring NH group of the compound of formula (IV) is protected eg with benzyl.

Pharmaceutically acceptable salts may be prepared conventionally by reaction with the appropriate acid or acid derivative.

Compounds of formula (I) and their pharmaceutically acceptable salts or solavtes thereof have Vanilloid receptor antagonist (VR1) activity and are believed to be of potential use for the treatment or prophylaxis of certain disorders, or treatment of the pain associated with them, such as: pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, respiratory diseases, asthma, cough, COPD, broncho constriction, inflammatory disorders, oesophagitis, heart burn, Barrett's metaplasia, dysphagia, gastroeosophageal relux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis (hereinafter referred to as the "Disorders of the Invention").

Accordingly, the invention also provides a compound of formula (I) or a pharmaceutically acceptable salt or solvate thereof, for use as an active therapeutic substance, in particular, in the treatment and/or prophylaxis of the Disorders of the Invention.

In particular, the invention provides a compound of formula (I) or a pharmaceutically acceptable salt or solvate thereof for use in the treatment or prophylaxis of pain.

The invention further provides a method for the treatment or prophylaxis of disorders in which antagonism of the Vanilloid (VR1) receptor is beneficial, in particular the Disorders of the Invention, in mammals including humans, which comprises administering to a mammal in need thereof a therapeutically effective amount of a compound of formula (I) or a pharmaceutically acceptable salt or solvate thereof.

The invention provides for the use of a compound of formula (I) or a pharmaceutically acceptable salt or solvate thereof in the manufacture of a medicament for the treatment or prophylaxis of disorders in which antagonism of the Vanilloid (VR1) receptor is beneficial, particularly the Disorders of the Invention.

In order to use the compounds of the invention in therapy, they will normally be formulated into a pharmaceutical composition in accordance with standard pharmaceutical practice. Thus, the present invention also provides a pharmaceutical composition, which comprises a compound of formula (I) or a pharmaceutically acceptable salt or solvate thereof and a pharmaceutically acceptable carrier or excipient therefor.

A pharmaceutical composition of the invention, which may be prepared by admixture, suitably at ambient temperature and atmospheric pressure, is usually adapted for oral, parenteral, rectal administration or intravesical adminstration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three a day, so that the total daily dosage is in the range of about 0.5 to 1000 mg; and such therapy may extend for a number of weeks or months.

No unacceptable toxicological effects are indicated with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

DESCRIPTION 1

3-Methyl-5-nitroisoquinoline (D1)

A solution of 3-methylisoquinoline (5.4 g, 0.04 mol) in concentrated sulfuric acid (30 ml) was cautiously added to a solution of potassium nitrate (4.25 g, 1.1 eq) in concentrated sulfuric acid (23 ml) whilst maintaining the temperature below 4° C. (ice bath). Stirring was continued for 2 h and then temperature raised to ambient. Reaction was further stirred for 3 h and then poured into ice-water slurry (500 mL. Neutralisation using solid potassium carbonate affored a yellow solid which was filtered and washed with water. This material was dissolved in ethanol (200 mL, filtered and concentrated under reduced pressure to afford the title compound as a yellow solid.

DESCRIPTION 2

3-Methyl-5-aminoisoquinoline (D2)

A solution of (D1) (1 g, 5.3 mM) and 10% palladium on charcoal (0.15 g) in methanol (40 ml) was hydrogenated at atmospheric pressure for 1 h. The catalyst was filtered off and the filtrate concentrated under reduced pressure to afford the product as a grey solid (0.64 g).

DESCRIPTION 3

1-(1-Benzyl-pyrrolidin-3-yl)-3-(3-methyl-isoquinolin-5-yl)urea (D3)

To a stirred solution of (D2) (1.50 g, 10.30 mmol) and pyridine (0.91 mL,1 1.30 mmol) in dichloromethane (50 mL) was added phenylchloroformate (1.42 mL, 11.30 mmol) dropwise at 25° C. over 10 min. After 1 h, triethylamine (1.58 mL, 11.30 mmol) was added and the reaction left to stir for a further 20 min. After this period, (R)—N-benzyl-3-aminopyrrolidine (1.67 g, 10.30 mmol) was added in dichloromethane (50 mL) and the whole stirred at 25° C. for 18 h. The mixture was then diluted with dichloromethane (100 mL), washed with water (100 ml) and dried ($Na_2SO_4$). Evaporation in vacuo gave a solid, which on recrystallisation from dichloromethane/petroleum ether gave the title compound as a pale brown solid (2.56 g). $^1$H NMR ($CDCl_3$) $\delta$ : 2.20-2.40 (3H, m), 2.45-2.50 (1H, m), 2.63 (3H, s), 2.70-2.80 (1H, m), 2.90-3.00 (1H, m), 3.50-3.60 (2H, m), 4.25-4.35 (1H, m), 5.35 (1H, d, J=8.1 Hz), 7.15-7.20 (2H, m), 7.25-7.30 (3H, m), 7.45-7.55 (2H, m), 7.77 (2H, d, J=7.3 Hz), 9.17 (1H, s).

DESCRIPTION 4

1-(3-Methyl-isoquinolin-5-yl)-3-pyrrolidin-3-yl urea (D4)

A solution of (D3) (2.30 g, 6.40 mmol), ammonium formate (2.02 g, 32.10 mmol) and 10% palladium on carbon (1 g) in methanol (100 mL) was heated at 70° C. for 3 h, then cooled to 25° C. and filtered through Celite. Evaporation in vacuo gave an oil which was suspended in dichloromethane and washed with saturated sodium carbonate solution. The organic layer was removed, dried ($Na_2SO_4$), and the solvents evaporated in vacuo to give the title compound as a yellow oil (1.2 g). $^1$H NMR ($CDCl_3$) δ: 2.05-2.20 (2H, m), 2.68 (3H, s), 2.85-2.95 (2H, m), 3.00-3.15 (2H, m), 4.35-4.45 (1H, m), 5.85-5.90 (1H, m), 7.40-7.50 (2H, m), 7.62 (1H, s), 7.72 (1H, d, J=8.2 Hz), 7.91 (1H, d, J=7.6 Hz), 9.14 (1H, s).

DESCRIPTION 5

5-Amino-1-methylisoquinoline (D5)

The title compound was prepared in a similar manner to that of K. C. Agrawal, B. A. Booth, A. C. Sartorelli, *J. Med. Chem.,* 1968 11 700.

DESCRIPTION 6

1-(1-tert Butyloxycarbonylazetidin-3-yl)-3-(1-methyl-isoquinolin-5-yl)urea (D6)

The title compound was prepared from 1-tert butyloxycarbonyl-3-aminoazetidine (synthesis described in WO 03/078438) in a similar manner to that described in D3. MH+ 357

DESCRIPTION 7

1-(1-Methyl-isoquinolin-5-yl)-3-azetidin-3-yl urea (D7)

The title compound was prepared from D6 by deprotection using trifluoroacetic acid in a similar manner to that described in WO 03/022809.

EXAMPLE 1

1-(3-Methyl-isoquinolin-5-yl)-3-[1-(2-trifluoromethyl-benzyl)pyrrolidin-3-yl]urea (E1)

A mixture of (D4) (40 mg, 0.15 mmol) and 2-trifluoromethyl benzaldehyde (23 mg, 0.13 mmol) in dichloromethane (5 ml) was stirred at 25° C. for 1 h. Sodium triacetoxyborohydride (32 mg, 0.15 mmol) was added and the reaction stirred for 48 h. A saturated solution of sodium hydrogen carbonate (5 mL) was added and the mixture stirred for 15min. The organic layer was removed, stirred with polymer supported isocyanate resin (2.1 eq.) for 3 h and then filtered. The filtrate was applied to an SCX column and eluted with methanol followed by 2% ammonia in methanol. Evaporation of the solvent in vacuo gave the title compound as a pale yellow solid (32 mg, 56%). $^1$H NMR ($CDCl_3$) δ: 2.25-2.35 (2H, m), 2.50-2.70 (3H, m), 2.62 (3H, s), 2.80-2.90 (1H, m), 3.67-3.75 (2H, m), 4.30-4.40 (1H, m), 5.35 (1H, d, J=8.1 Hz), 7.25-7.40 (3H, m), 7.45-7.55 (4H, m), 7.70-7.80 (2H, m), 9.16 (1H, s); MS: $C_{23}H_{23}N_4OF_3$ requires 428, found 429 (MH$^+$).

The compounds listed in Tables 1 & 2 below and Example 25 were prepared methods similar to those described above.

TABLE I

| Ex | Structure | MS |
| --- | --- | --- |
| 2 | 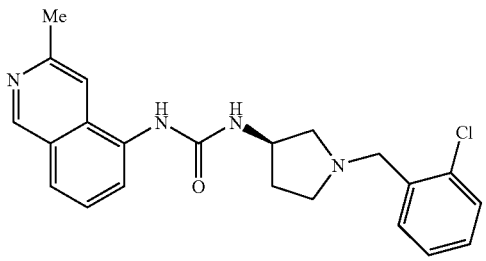 | $C_{22}H_{23}N_4OCl$ requires 394/396<br>Found 395/397 (MH$^+$) |
| 3 | 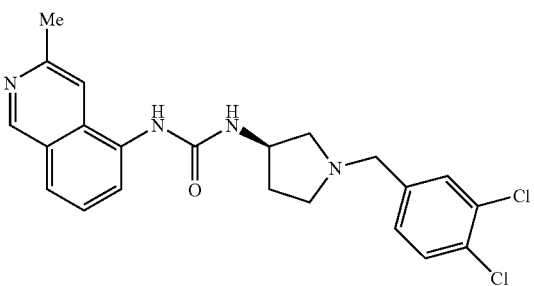 | $C_{22}H_{22}N_4OCl_2$ requires 428/430<br>Found 429/431 (MH$^+$) |

TABLE I-continued

| Ex | Structure | MS |
|---|---|---|
| 4 | (3-methylisoquinolin-5-yl)-urea-pyrrolidinyl-(3-fluorobenzyl) | C₂₂H₂₅N₄OF requires 378<br>Found 379 (MH⁺) |
| 5 | (3-methylisoquinolin-5-yl)-urea-pyrrolidinyl-(3,4-difluorobenzyl) | C₂₂H₂₂N₄OF₂ requires 396<br>Found 397 (MH⁺) |
| 6 | (3-methylisoquinolin-5-yl)-urea-(2-methylpyrrolidinyl)-(2-trifluoromethylbenzyl) | C₂₄H₂₅N₄OF₃ requires 442<br>Found 443 (MH⁺) |
| 7 | (3-methylisoquinolin-5-yl)-urea-pyrrolidinyl-(3-chloro-5-trifluoromethylpyridin-2-yl)methyl | C₂₂H₂₁ClF₃N₅O requires 463<br>Found 463, 465 (MH⁺) |

TABLE 2

Examples 8-24 are defined by the following formula:

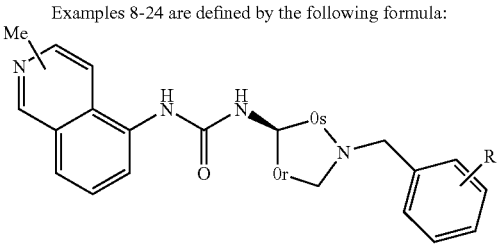

(R may represent 1 or 2 substituents as shown in the table)

| Ex | Me posn | R | r | s | MS (MH+) |
|----|---------|------|---|---|----------|
| 8  | 3-      | H    | 1 | 1 | 361      |
| 9  | 3-      | 2-F  | 1 | 1 | 379      |
| 10 | 3-      | 4-F  | 1 | 1 | 379      |
| 11 | 3-      | 4-CN | 1 | 1 | 386      |
| 12 | 3-      | 4-Cl | 1 | 1 | 395, 397 |
| 13 | 3-      | 3-Cl, 4-F | 1 | 1 | 447, 449 |
| 14 | 3-      | 3-Cl | 1 | 1 | 395, 397 |
| 15 | 3-      | 4-t-Bu | 1 | 1 | 417    |
| 16 | 3-      | 3-CF$_3$ | 1 | 1 | 429   |
| 17 | 3-      | 4-CF$_3$ | 1 | 1 | 429   |
| 18 | 3-      | 2-CN | 1 | 1 | 386      |
| 19 | 3-      | 3-CN | 1 | 1 | 386      |
| 20 | 1-      | 2-F  | 0 | 1 | 365      |
| 21 | 1-      | 2,3-diF | 0 | 1 | 383   |
| 22 | 1-      | 2-CF$_3$ | 0 | 1 | 415   |
| 23 | 1-      | 3-CF$_3$ | 0 | 1 | 415   |
| 24 | 1-      | 4-CF$_3$ | 0 | 1 | 415   |

| 25 | 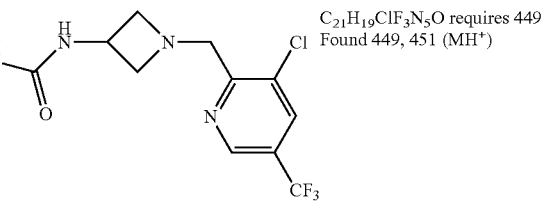 | $C_{21}H_{19}ClF_3N_5O$ requires 449<br>Found 449, 451 (MH+) |
|----|---|---|

Pharmacological Data

(a) In vitro Assay

As referenced above, the compounds of the invention are vanilloid receptor (VR1) antagonists and hence have useful pharmaceutical properties. Vanilloid receptor (VR1) antagonist activity can be confirmed and demonstrated for any particular compound by use of conventional methods, for example those disclosed in standard reference texts such as D. Le Bars, M. Gozarin and S. W. Cadden, Pharmacological Reviews, 2001, 53(4), 597-652] or such other texts mentioned herein.

The screen used for the compounds of this invention was based upon a FLIPR based calcium assay, similar to that described by Smart et al. (British Journal of Pharmacology, 2000, 129, 227-230). Transfected astrocytoma 1321N1 cells, stably expressing human VR1, were seeded into FLIPR plates at 25,000 cells/well (96-well plate) and cultured overnight.

The cells were subsequently loaded in medium containing 4 μM Fluo-3 AM (Molecular Probes) for 2 h, at room temperature, in the dark. The plates were then washed 4 times with Tyrode containing 1.5 mM calcium, without probenecid. The cells were pre-incubated with compound or buffer control at room temperature for 30 min. Capsaicin (Sigma) was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium concentration resulting in fluorescence. A compound having antagonist activity blocks the capsaicin binding to the receptor, there is no signalling and therefore no increase in intracellular calcium levels and consequently lower fluorescence. pKb values are generated from the IC$_{50}$ values using the Cheng-Prusoff equation.

All compounds (Examples 1-25) tested by the above methodology had pKb>6, preferred compounds (Examples 1-6, 13-14, 16-17, 22) having a pKb>7.0.

(b) FCA-Induced Hyperalgesia in the Guinea Pig 100 ul of 1 mg/ml FCA was injected intraplantar into the left paw of 4 groups of 8 male Dunkin Hartley guinea-pigs (batch: 6282434, average weight 340 g). 24 h later compounds were administered orally at 0 (vehicle), 3, 10 30 mg/kg with vehicle as 1% methylcellulose and dosing volume being 2 ml/kg and dosing straight into the stomach. The methylcellulose was added gradually to the compound into the pestle and mortar and ground together.

Behavioural readouts of mechanical hyperalgesia were obtained before FCA administration (naïve reading), after FCA but before drug administration (predose reading) and 1 hour after drug administration. The readout used was paw pressure (Randall-Sellito) and the end point was paw withdrawal. The paw pressure equipment also had one silver disc placed on the point to increase the markings by a factor of 2.

Compounds having a pKb>7.0 in vitro, according to model (a) above, were tested in this model and shown to be active.

The invention claimed is:

1. A compound of formula (I):

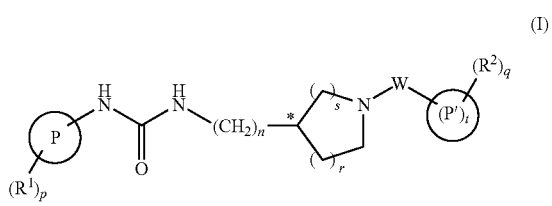

(I)

or a pharmaceutically acceptable salt thereof, wherein:
P is 5-isoquinolinyl;
P' is phenyl or pyridyl;
$R^1$ and $R^2$ are independently selected from the group consisting of —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)₂NR⁴R⁵, —OS(O)₂R⁶, —OS(O)₂CF₃, —O(CH₂)ₓNR⁴R⁵, —C(O)CF₃, —C(O)alkyl, —C(O)cycloalkyl, —C(O)aralkyl, —C(O)Ar, —C(O)(CH₂)ₓOR⁶, —C(O)(CH₂)ₓNR⁴R⁵, —C(O)alkoxy, —C(O)NR⁴R⁵, —(CH₂)ₓC(O)alkoxy, —(CH₂)ₓOC(O)R⁶, —(CH₂)ₓOR⁶, —(CH₂)ₓNR⁴R⁵, —(CH₂)ₓC(O)NR⁴R⁵, —(CH₂)ₓN(R⁴)C(O)R⁶, —(CH₂)ₓS(O)₂NR⁴R⁵, —(CH₂)ₓN(R⁴)S(O)₂R⁶, -ZAr, —(CH₂)ₓS(O)₂R⁶, —(OCH₂)ₓS(O)₂R⁶, —N(R⁴)S(O)₂R⁶, —N(R⁴)C(O)R⁶ or
—(CH₂)ₓC(O)alkyl;

R⁴ and R⁵ may be the same or different and represent H or alkyl or R⁴ and R⁵ together with the nitrogen atom to which they are attached form a C₃₋₆azacycloalkane, or a C₃₋₆(2-oxo)azacycloalkane ring;

Z represents O, S or NR⁷;
W represents a group CHR³ or (CH₂)CHR³;
R³ represents hydrogen or alkyl;
R⁶ represents alkyl or phenyl;
R⁷ represents hydrogen, alkyl or phenyl;
m represents an integer 1 or 2;
n represents an integer 0, 1, 2 or 3;
p and q independently represent an integer 0, 1, 2, 3 or 4;
r represents an integer 0 or 1;
s represents 1;
t represents 1; and
x represents an integer 0, 1, 2, 3, 4, 5 or 6.

2. A compound according to claim 1 or a pharmaceutically acceptable salt thereof wherein W represents CHR³, where R³ is H or methyl.

3. A compound according to claim 2 which is a compound of formula (IA):

(IA)

or a pharmaceutically acceptable salt thereof, wherein:
X represents CH or N; n represents 0; p represents 1 and q represents 0, 1, or 2.

4. A compound according to claim 3 or a pharmaceutically acceptable salt thereof wherein X represents CH.

5. A compound according to claim 3 or a pharmaceutically acceptable salt thereof wherein R¹ represents methyl.

6. A compound according to claim 5 or a pharmaceutically acceptable salt thereof wherein r is 1 and s is 1.

7. A compound according to claim 5 or a pharmaceutically acceptable salt thereof wherein r is 0 and s is 1.

8. A compound according to claim 5 or a pharmaceutically acceptable salt thereof wherein R² represents H, halo or CF₃.

9. A compound according to claim 5 or a pharmaceutically acceptable salt thereof wherein q represents 1 or 2.

10. A compound of claim 3 which is represented by the following formula:

or a pharmaceutically acceptable salt thereof, wherein R¹ represents 1- or 3-methyl; R² is selected from the group consisting of F, CN, Cl, t-butyl, or CF₃; and q represents 1 or 2.

11. The compound of claim 10 or a pharmaceutically acceptable salt thereof, wherein r and s each represent 1.

12. The compound of claim 10 or a pharmaceutically acceptable salt thereof, r represents 0 and s represents 1.

13. The compound of claim 1 which is represented by the following compound:

or a pharmaceutically acceptable salt thereof.

14. A pharmaceutical formulation comprising a compound of claim 1 or a pharmaceutically acceptable salt thereof together with a pharmaceutically acceptable carrier or excipient.

15. A method of treatment or prophylaxis of pain which comprises administering to a patient a compound of formula (I) according to claim 1.

* * * * *